United States Patent [19]

Feller, Jr. et al.

[11] 4,362,156
[45] Dec. 7, 1982

[54] INTRAVENOUS INFUSION ASSEMBLY

[75] Inventors: John Feller, Jr., Vandalia; Stanley C. Wells, Jr., Centerville, both of Ohio

[73] Assignee: Riverain Corporation, Dayton, Ohio

[21] Appl. No.: 31,306

[22] Filed: Apr. 18, 1979

[51] Int. Cl.³ .............................................. A61M 5/00
[52] U.S. Cl. .................................... 604/165; 604/177
[58] Field of Search ................ 128/214 R, 214.4, 221, 128/347, DIG. 16

[56] References Cited

U.S. PATENT DOCUMENTS

| | | | |
|---|---|---|---|
| 3,064,648 | 11/1962 | Bujan | 128/214 R |
| 3,094,122 | 6/1963 | Gauthier et al. | 128/214.4 |
| 3,454,006 | 6/1971 | Loper et al. | 128/214.4 |
| 3,454,006 | 7/1969 | Langdon | 128/214.4 |
| 3,459,183 | 8/1969 | Ring et al. | 128/214.4 |
| 3,592,192 | 7/1971 | Harautuneian | 128/214.4 |
| 3,680,562 | 8/1972 | Wittes et al. | 128/347 |
| 3,714,945 | 2/1973 | Stanley | 128/214.4 |
| 3,727,613 | 4/1973 | Sorenson et al. | 128/214.4 |
| 3,769,975 | 11/1973 | Nimoy et al. | 128/214.4 |
| 3,774,604 | 11/1973 | Danielsson | 128/214.4 |
| 3,782,383 | 1/1974 | Thompson et al. | 128/214.4 |
| 3,827,434 | 8/1974 | Thompson et al. | 128/214.4 |
| 3,860,006 | 1/1975 | Patel | 128/347 |
| 3,906,946 | 9/1975 | Nordstrom | 128/214.4 |
| 3,923,066 | 12/1975 | Sausse et al. | 128/348 |
| 3,934,576 | 1/1976 | Danielsson | 128/214 R X |
| 4,015,600 | 7/1975 | Liautaud | 128/214 R |
| 4,016,879 | 4/1977 | Mellor | 128/214.4 |
| 4,020,835 | 5/1977 | Nordstrom et al. | 128/214.4 |
| 4,079,738 | 3/1978 | Dunn et al. | 128/214.4 |
| 4,177,809 | 12/1979 | Moorehead | 128/214.4 |
| 4,192,305 | 3/1980 | Seberg | 128/214.4 |
| 4,198,973 | 4/1980 | Millet | 128/214.4 |
| 4,231,367 | 11/1980 | Rash | 128/214.4 |

FOREIGN PATENT DOCUMENTS 77010 11/1948 Czechoslovakia ............ 128/214.4

*Primary Examiner*—Dalton L. Truluck
*Attorney, Agent, or Firm*—Biebel, French & Nauman

[57] ABSTRACT

A flexible, winged, over-the-needle catheter assembly and a needle assembly are releasably locked together at their distal ends to prevent relative axial movement therebetween during insertion into a vein. After insertion, the needle assembly can be easily unlocked and then retracted from the catheter assembly. Relative rotation between the catheter and the needle assemblies is prevented by interfitting surfaces thereon, and the direction that the needle bevel faces is indicated by indicia on the catheter wings.

10 Claims, 4 Drawing Figures

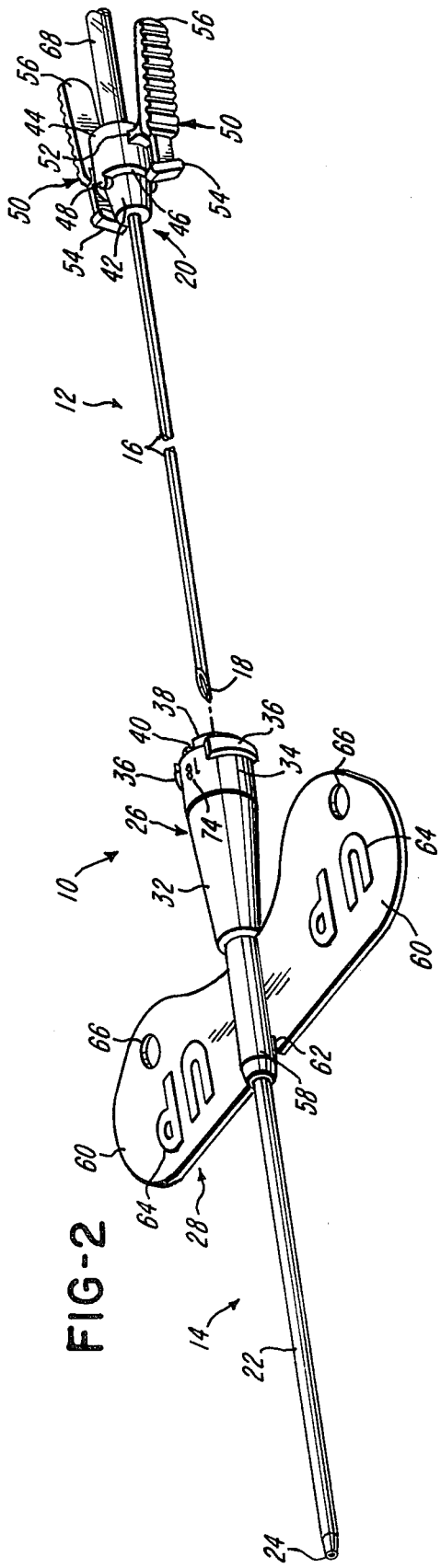
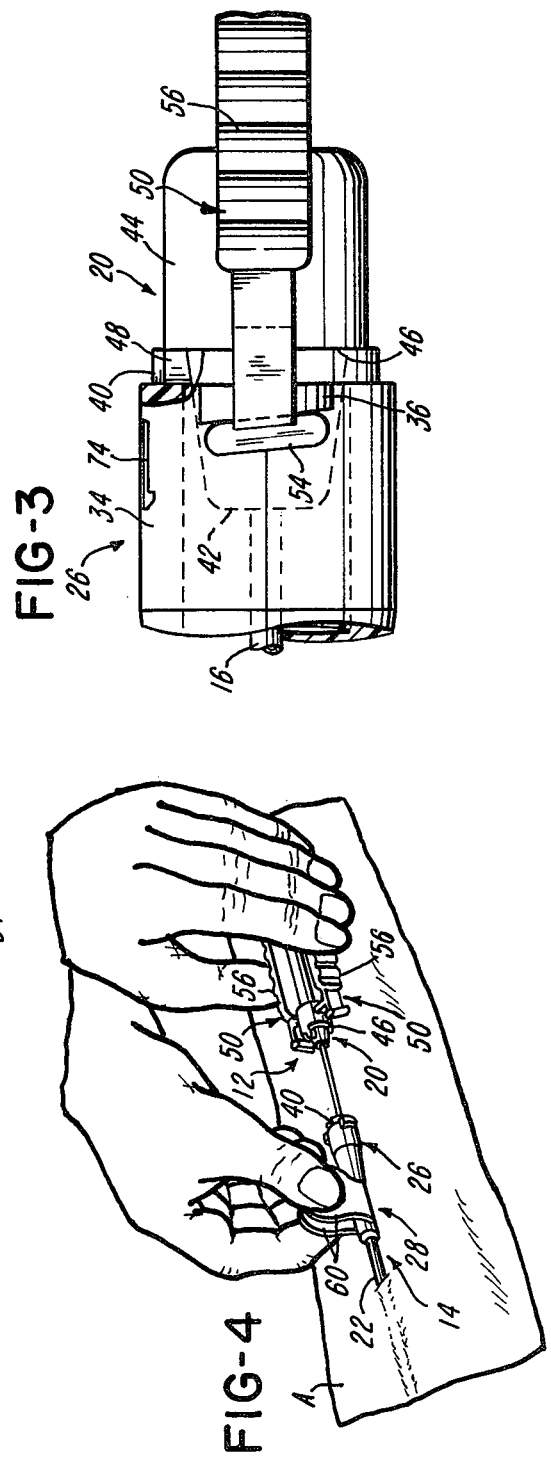
FIG-2  FIG-3  FIG-4

INTRAVENOUS INFUSION ASSEMBLY

BACKGROUND OF THE INVENTION

This invention relates to an intravenous infusion assembly and more particularly to an infusion assembly for intravenous administration of fluids into small veins at areas of the body difficult to reach, such as scalp veins of an infant. However, an infusion assembly of this invention may advantageously be used for other purposes, as will be apparent to those familiar with the art.

Intravenous infusion assemblies in common use today employ so-called "winged" needles that include flexible plastic wings rigidly connected to small, metal needles and so designed that one may grip the wings, squeezing them between the thumb and forefinger, to assist in accurately positioning the needle and pushing it into the desired vein. U.S. Pat. No. 3,064,648, granted to Bujan on Nov. 20, 1962, illustrates a needle assembly of this type.

Those who use such needle assemblies have found them to be convenient and relatively easy to apply. However, since the metal needle is sharp pointed and rigid, relatively small movements of the needle after application and while in place in a vein may rupture the vein and permit the infusion fluid to infiltrate adjacent tissue. Because rupture of the vein is a likely occurrence, winged needle assemblies are more typically used only for short periods of time.

Needle and catheter sets of the type wherein the needle is inside a flexible catheter, such as shown in U.S. Pat. No. 3,094,122, issued Jan. 18, 1963, to Gauthier et al, possess substantial advantages, especially for use when infusion is to take place over an extended period of time. Their greatest advantage, of course, is that the flexible catheter is supported by the needle only during insertion into a vein and is all that remains in the vein. Unlike a needle, such a catheter is not rigid, does not have a sharp point and is not as likely to rupture the vein as a result of minor relative movements between the infusion assembly and the vein. However, such catheter and needle sets are not as convenient to administer in difficult locations because they are designed to be gripped from the rear, and thus one cannot control the position of the point of the needle with the ease and accuracy of the aforementioned devices having wings on needles.

A slidably mounted wing assembly on an over-the-needle catheter is described in U.S. Pat. No. 3,589,361, issued to Loper et al on June 29, 1971. However, it appears that the Loper device would be expensive to manufacture and cumbersome to use. So far as known, the device has not been generally accepted.

SUMMARY OF THE INVENTION

In accordance with this invention, an intravenous infusion assembly is provided comprising a cannula or needle assembly and a catheter assembly. The catheter assembly includes a catheter and a gripping assembly in the form of flexible wings effectively hinged to the catheter. Each of the needle assembly and the catheter assembly is provided with a hub and means are provided for releasably locking the hubs together so that one holding the gripping assembly connected to the catheter may, in effect, by way of the locking means, pull the cannula or needle along with the catheter assembly to insert the needle into a vein. An infusion assembly of this invention may be inserted with substantially the same ease and accuracy as s winged needle assembly.

After an infusion assembly of this invention is inserted into a vein, the needle and catheter hubs may be unlocked by the operation of lock release means associated with the locking means. The lock release means is so constructed that the locking means is disabled by quite natural movements of the thumb and forefinger occurring from the act of gripping the needle hub. After the hubs are unlocked, the catheter assembly can be held in place and the needle assembly removed.

Flashback means is provided to indicate that the infusion assembly is properly located in a vein by the flow of blood from the vein into the flashback means, the flashback means being connected to the needle hub so that it is removed from the catheter assembly when the needle assembly is removed.

For ease in manufacture and to enhance the appearance of the infusion assembly of this invention, the needle and catheter hubs are substantially symmetrical about, and coaxial with, the common longitudinal axis of the needle and the catheter. As conventional, the distal end of the needle is formed with a sharp point by bevel grinding. One normally wants the beveled surface to face away from the skin when it is to be punctured and will think of the skin as being "down" so that the beveled surface faces "up." This alignment of the beveled surface is indicated by marking the catheter wings, which have a natural orientation that is perpendicular to the aforementioned "up" direction, with the legend "UP" facing the same direction that the beveled surface faces. In order to maintain this relationship, means interfitting the needle hub and the catheter hub are provided to prevent relative rotation between the needle and catheter assemblies.

The primary object of this invention is to provide an improved, inexpensive and easy-to-use intravenous infusion assembly. Other objects and advantages are apparent from the foregoing summary and will become apparent from the following description.

THE DRAWINGS

FIG. 2 is an exploded perspective view of the assembly of FIG. 1.

FIG. 3 is an enlarged side elevational view with parts broken away of a portion of the assembly of FIG. 1.

FIG. 4 is a partial perspective view illustrating a procedure for removing the needle assembly after the infusion assembly is applied to a patient.

DESCRIPTION OF THE PREFERRED EMBODIMENTS

Figure 1:
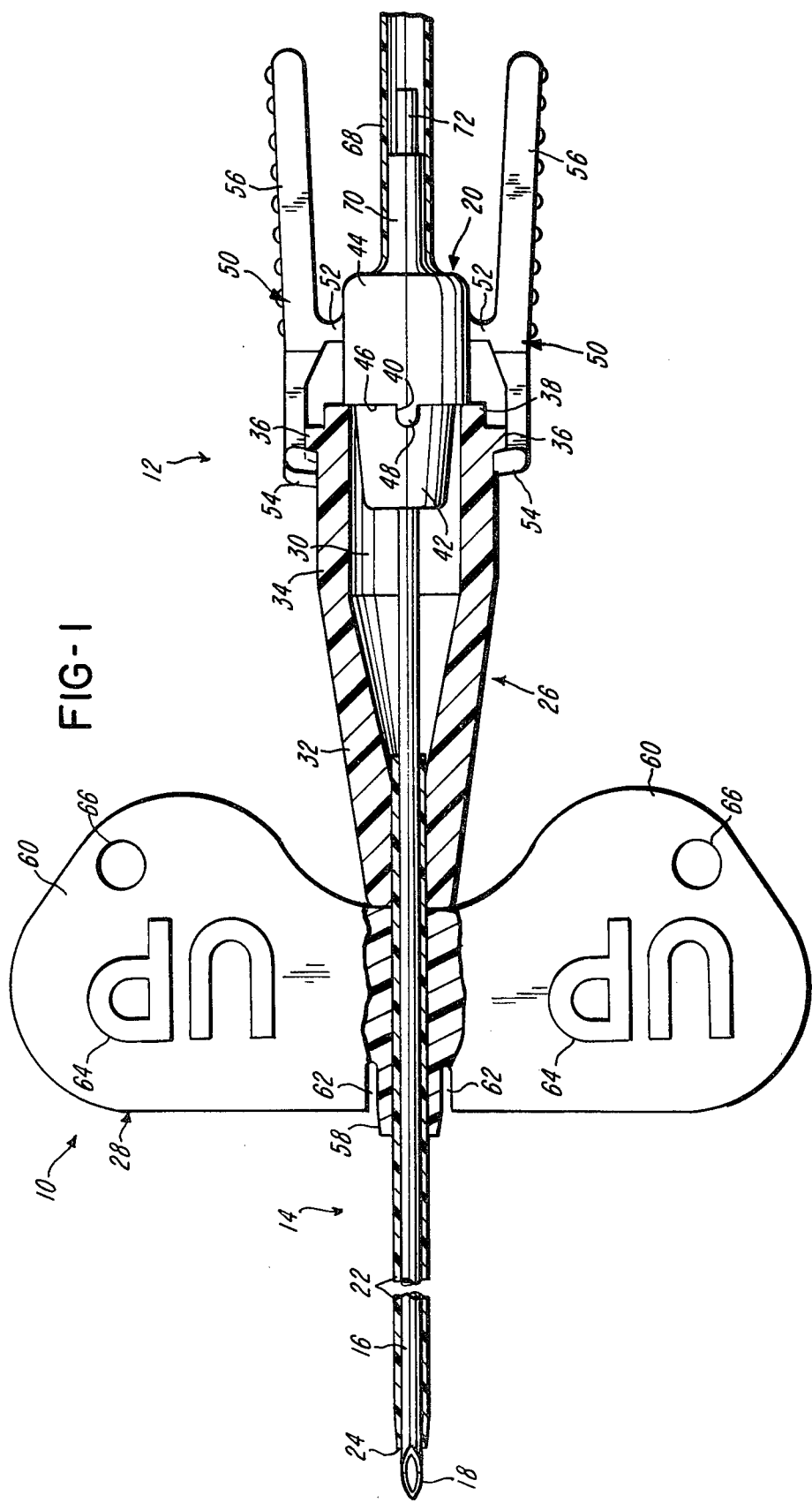
FIG. 1 is a plan view of an intravenous infusion assembly in accordance with this invention, parts being broken away and parts shown in cross-section.

With reference to FIGS. 1 and 2, an intravenous infusion assembly, generally designated 10, in accordance with this invention comprises a needle assembly 12 and an over-the-needle catheter assembly 14.

The needle assembly 12 comprises an elongate, hollow metal cannula or needle 16 adapted to be inserted through the skin and into a vein. For ease in puncturing the skin, the free or distal end of the needle 16 is conventionally beveled as indicated at 18 to form a sharp point. The opposite or proximal end of the needle 16 is rigidly affixed to a needle hub, generally designated 20.

The catheter assembly 14 includes an elongate, tubular, hollow, flexible, thin-walled catheter 22 having a tapered, reduced diameter free or distal end 24. The opposite, proximal end of the catheter 22 is fixedly connected to a catheter hub generally designated 26. A catheter gripping assembly, generally designated 28, is fixedly connected to the catheter 22 intermediate to its distal end 24 and the hub 26.

Catheter hub 26 comprises a hollow, one-piece, molded plastic body having a central cavity 30 opening to its rearward end and formed from a generally conical distal or forward body portion 32 and a generally cylindrical proximal or rearward body portion 34. The outer surface of the distal body portion 32 tapers outwardly and rearwardly to join with the outer surface of the proximal body portion 34. The distal end of the catheter hub 26 snugly receives the proximal end of the catheter 22 and is fixedly joined thereto. Preferably, the catheter 22 is preformed as an extrusion and then the catheter hub 26 is molded directly onto the catheter 22.

The proximal end of the catheter hub 26 is provided with radially and circumferentially extending lugs that may be used with conventional equipment employing Luer locks for external connection to a source of infusion fluid. The extreme proximal end of the catheter hub 26 is formed as a reduced diameter portion 38 so that it may be compatible with the connection equipment. For reasons to be described below, the reduced diameter end portion 38 is provided with a rearwardly opening locating notch 40.

Needle hub 20 comprises a one-piece, molded plastic body having a distal or forward body portion 42 and a proximal or rearward body portion 44. The distal body portion 42 has a truncated conical configuration with an outwardly and rearwardly sloping outer surface. Its rearward end forms a base of smaller diameter than the proximal body portion 44 so that the forward end of the proximal body portion 44 forms a distally facing shoulder 46 surrounding the distal body portion 42. The needle hub 20 is preferably molded rigidly to the needle 16 using conventional techniques.

The needle assembly 12 and the catheter assembly 14 are adapted to be assembled with the catheter over the needle, as shown in FIG. 1, by advancement of the needle 16 through the catheter hub 26 and the catheter 22. As the needle 16 nears full insertion into the catheter 22, the distal body portion 42 of the needle hub 20 is guided by its sloping outer surface into the catheter hub cavity 30. When fully inserted, the distally facing shoulder 46 of the needle hub abuts the rear face of the catheter hub 26, and a needle hub tenon 48 that projects forwardly from the shoulder 46 seats within the locating notch 48. Accordingly, the interfitting tenon 48 and notch 40 cooperate to prevent relative rotation between the needle assembly 12 and the catheter assembly 14. They also serve to align the assemblies in preparation for use, as will be further described below.

To obtain proper spacing between the extreme distal ends of the needle 16 and the catheter 22, it may be observed in FIG. 1 that the extension of the needle 16 distally of the shoulder 46 is slightly greater than the overall length of catheter assembly 14. As common, the distal end 24 of the catheter 22 is preferably necked down to frictionally engage the shank of the needle 16, other parts of the catheter 22 having an internal diameter slightly greater than the outer diameter of the needle 16. The internal diameter of the catheter hub proximal body portion 34 is also greater than the greatest diameter of the needle hub distal body portion 42. With this construction, the tapered distal end 24 of the catheter 22 will follow along with the needle distal end 18 into a vein, resistance to relative movement between the needle 16 and the catheter 22 being provided by the friction between the distal end surfaces of the needle and the catheter.

Relative axial movement of the assembled needle assembly 12 and catheter assembly 14, when they are inserted through the skin and into a vein, is prevented by releasably locking means comprising a pair of clamp arms 50 connected by integral hinges 52 to the proximal body portion 44 of the catheter hub 20. The arms 50 project forwardly of the hinges 52 and terminate in hooks 54, the rearwardly facing surfaces of which are formed to confront and mate with the forwardly facing surfaces of the lugs 36. Preferably, the clamp arms 50, as molded, tend to occupy substantially the position thereof shown in FIG. 1 so that, when the parts are assembled, the hooks 54 will inherently be biased into clamping engagement with the lugs 36. The arms 50 further include ribbed lock release or finger grips 56 extending rearwardly of the hinges 52. To initiate removal of the needle assembly 12 from the catheter assembly 14, one simply engages the respective finger grips 56 with the thumb and forefinger and, with a squeezing motion, moves them toward one another and thereby releases the hooks 54 from engagement with the lugs 36.

The catheter gripping assembly 28 comprises a tubular, central body member 58 that is fixed to and coaxially surrounds the catheter 22 and further comprises a pair of opposed, substantially co-planar catheter wings 60 that are integrally molded in one piece with the body member 58. The wings 60 are constructed of sufficiently flexible material that they may be bent or folded adjacent to the tubular body member 58 whereupon their upper surfaces can be brought into face-to-face contact with one another. They are also sufficiently resilient that, when relesed, they will return to their relaxed, as molded, positions thereof illustrated in FIGS. 1 and 2.

One may insert the infusion assembly 10 through the skin and into a vein while the needle assembly 12 is locked to the catheter assembly 14 by bending, gripping and pulling or pushing the wings 60. In effect, the catheter assembly 14 pulls the needle assembly 12 with it due to the fact that the catheter and needle hubs are locked together. After inserting the needle and the catheter into the vein and while still maintaining a grip on the wings 60 as illustrated in FIG. 4, one may manually engage the finger grips 56 to release the lock between the needle hub 20 and the catheter hub 26 and then retract the needle assembly 12. FIG. 4 illustrates a convenient mode of needle retraction wherein the needle assembly 12 is held and moved by the left hand while the catheter assembly 14 is held by the right hand in fixed position on the arm A of a patient. The initial rearward movement of the needle assembly 12 is slightly resisted due to the frictional engagement of the distal ends of the needle 16 and catheter 22. When this resistance is overcome, the needle assembly 12 can be retracted without any further substantial resistance.

Although the wings 60 are located relatively close to the distal end of the needle 16 and are conveniently located and usable for applying the infusion assembly by in effect pushing on the distal end of the needle 16 while pulling the needle hub 20, there are those that may prefer to push the entire infusion assembly into the vein by gripping the clamp arms 50. For reasons mentioned above, the clamp arms 50 and the hinges 52 are so designed that one, in gripping them, will release the locking engagement between the hooks 54 and the lugs 36. However, the arms 50 can be gripped and one may, by pushing from the proximal end of the infusion assembly, puncture the skin and cause the needle 16 and the catheter 22 to enter a vein even though the hubs 20 and 26 are not locked together. After the infusion assembly is satisfactorily located within a vein, one may hold onto the catheter assembly 14 in any suitable fashion, preferably by gripping the wings 60 as illustrated in FIG. 4, and proceed to remve the needle assembly 12 by pulling rearwardly on the needle hub 20 without changing the grip on the finger grips 56.

Different individuals may adopt different procedures for removing the needle assembly 12 from the catheter assembly 14. Accordingly, there is no assurance that the wings 60 will be folded to the postion illustrated in FIG. 4 at the time the needle assembly 12 is removed. As previously indicated, the internal diameter of the catheter 22 throughout substantially its entire length should be slightly greater than the outer diameter of the needle 16 to minimize resistance to removal of the needle assembly 12. Therefore, the wings 60 and their connection to the central body member 58 should be sufficiently flexible that they may occupy the position shown in FIG. 2 or the position shown in FIG. 4, and all intermediate positions, without substantially distorting the shape of the catheter 22. As an accommodation, slots such as those indicated at 62, may interrupt the connection between the wings 60 and the tubular body member 58 to render the connection therebetween more flexible. As those familiar with the art will be aware, the slots 62 also cooperate with the distal end of the body member 58 and the confronting surfaces of the wings 60 to provide a socket for frictionally receiving the proximal end of a tubular sheath (not shown) used to protect the catheter and the needle during shipment and handling preparatory for use.

For ease in molding the various parts and to enhance the appearance of the infusion assembly 10, the several parts of the assembly are substantially symmetrical about, and coaxial with, the longitudinal axis of the needle and the catheter. However, infusion assemblies of this type have a distinct upper side and a lower side, it being a matter of importance that the beveled surface of the distal end 18 of the needle 16 face upwardly, i.e., away from the skin, in preparation for penetration into the skin. The upper surfaces of the wings 60 may conveniently be molded or otherwise provided with the legend "UP" as shown at 64 or other indicia indicating the upward direction corresponding generally to the direction in which the beveled surface of the needle 16 faces to assist one in orienting the infusion assembly 10 prior to inserting it into the skin. The upward orientation of the surfaces bearing the indicia 64 and the beveled surface of the needle 16 is maintained by the interfit between the locating notch 40 and the tenon 48.

It will be observed that, so long as the tenon 48 interfits the notch 40, the hinges 52 provide for a pivotal mounting of the clamp arms 50 for rotation about vertical axes that are parallel to the vertical plane extending through the longitudinal axis of the needle 16 and the catheter 22. (The term "vertical" as used herein refers to a direction generally perpendicular to the portion of the skin to be penetrated by the infusion assembly.) Because of this orientation of the clamp arms 50, one may, by quite natural movements of the thumb and forefinger, readily engage the finger grips 56 by essentially horizontal movements of the thumb and forefinger toward one another to effect clamp release.

Either before or after removal of the needle assembly 12, the wings 60 may be laid flat against the skin and taped thereto to retain the catheter assembly 14 in place for the duration of the infusion procedure. If desired, the wings 60 may be sutured to the skin, suture holes 66 being provided for this purpose.

The wings 60 are molded to lie in a horizontal plane, i.e., a plane perpendicular to the aforedescribed vertical direction, and are located generally on the underside of the tubular body member 58. Howver, it is believed that the points of connection of the wings 60 to the tubular body member 58 may satisfactorily be other than as illustrated in the drawings. For example, the wings 60 could lie in a plane extending diametrically through the longitudinal axis of the infusion assembly 10. The illustrated location of the wings 60 beneath such axis is presently preferred because wings so located, when held in face-to-face contact as shown in FIG. 4, provide firm control over the position of the needle 16 and the catheter 22.

Flashback chambers are conventionally provided to enable an attendant applying an infusion assembly to detect whether the needle and the catheter are properly placed within a vein by observing the flow of blood from the vein into the flashback chamber. A conventional flashback chamber could be provided on the rearward end of the needle hub 20. The illustrated infusion assembly 10 includes a flashback arrangement provided by means of an elongate, open ended, hollow plastic tube 68 into which blood may be collected. One end of the tube 68 may be connected to a rearwardly extending, hollow tubular support 70 that is preferably molded integrally with the needle hub 20. The extreme proximal or rearward end, designated 72, of the needle 16 preferably projects rearwardly from the hollow support tube 70 into the blood collection tube 68.

The catheter gauge may conveniently be marked as indicated by the indicia "18" at 74 on the upwardly facing surfce of the catheter hub 26.

Various materials may be used to mold the non-metallic parts of the needle assembly 12 and the catheter assembly 14. For example, the needle hub 20, clamp arms 50 and integral hinges 52 may be inexpensively molded in one piece from various plastic materials, ABS being an example. However, polypropylene is the material of choice primarily because integral hinges are easily formed from polypropylene. The catheter 22 may be made, preferably by extrusion, from a biocompatible grade of polyvinylchloride or polytetrafluoroethylene (Teflon), but a flexible and resilient polyurethane material is presently preferred. The catheter hub 26 and the gripping assembly 28 may also be made from various plastic materials. Particularly, the gripping assembly 28 could be made from the same type of material as the catheter 22. The catheter hub 26 must be fairly rigid and could be made from various plastic materials, examples including polypropylene, ABS, polyvinylchoride, and high density polyethylene. A fairly rigid polyurethane compound is preferred for ease in molding, especially if the catheter 22 is made from polyurethane.

Various manufacturing procedures could be used to produce the catheter assembly 14. Presently, it is preferred that both the catheter hub 26 and the gripping assembly 28 be molded directly onto the catheter 22 to be bonded thereto with the catheter hub 26 being molded before the gripping assembly 28. Also, the tubular body member 58 is preferably bonded, when molded, to the distal end of the catheter hub 26 to provide a direct transmission of motion from the gripping assembly 28 to the hub 26 while the needle 16 is being inserted into the skin.

Although the presently preferred embodiment of this invention has been described, it will be understood that, within the purview of this invention, various changes may be made within the scope of the appended claims.

We claim:

1. An infusion assembly comprising:
a needle assembly comprising a hollow needle and a needle hub rigidly connected to said needle;
an over-the-needle catheter assembly comprising a catheter, and a catheter hub fixedly connected to said catheter;
a gripping assembly comprising a pair of wings flexibly connected to said catheter assembly having a relaxed condition wherein they extend generally transversely to the longitudinal axis of said catheter assembly, said wings and their connection to said catheter assembly being sufficiently flexible that they may be gripped by the thumb and forefinger and brought into face-to-face engagement with one another without substantial distortion of said catheter;
releasable locking means comprising a pair of clamp arms fixed to said needle hub by pivot means, said clamp arms being on opposite sides of an upwardly directed plane containing the longitudinal axis of said needle and including engaging members on said clamp arms for engging parts fixed to said catheter hub and thereby connecting and preventing relative axial movement between said needle assembly and said catheter assembly with said needle extending through said catheter so that one may, by gripping said wings, move said catheter assembly and said needle assembly together for insertion of said needle and said catheter into a vein, said locking means being releasable without relative movement between said catheter assembly and said needle assembly, so that one may, following such insertion and upon release of said locking means, retract said needle assembly from said catheter assembly and the vein so that only said catheter remains in the vein;
interfitting means on said needle hub and said catheter hub preventing relative rotation therebetween when said needle assembly and said catheter assembly are connected by said locking means, said interfitting means establishing an alignment between said catheter assembly and said needle assembly such that upwardly facing surfaces of said wings face the same direction as the upwardly facing surfaces of said needle so that said wings are on opposite sides of said upwardly directed plane containing the longitudinal axis of said needle; and
said needle hub comprising a body having a distally facing surface abutting the proximal end of said catheter hub when said needle assembly and said catheter assembly are connected together.

2. The infusion assembly of claim 1 wherein said surfaces on said hubs comprise a notch on one of said hubs and a tenon on the other of said hubs adapted to interfit within said notch.

3. The infusion assembly of claim 1 wherein said needle hub and said clamp arms fixed to said needle hub are integrally molded in one piece.

4. The infusion assembly of claim 3 wherein said pivot means are hinges and said clamp arms are mounted on said needle hub by said hinges for rotation about substantially vertical axes and said finger grips are so located that one gripping said needle hub will naturally tend to engage said finger grips to disable said locking means.

5. The infusion assembly of claim 1 wherein the distal end of said needle has a beveled surface and wherein said wings are provided with indicia indicating an upward orientation facing generally the same direction as said beveled surfaces.

6. The infusion assembly of claim 1 wherein said catheter, said catheter hub and said wings are joined together by molding said catheter hub and said wings onto said catheter.

7. The infusion assembly of claim 1 wherein said catheter is made from a flexible, resilient polyurethane plastic.

8. The infusion assembly of claim 2 wherein said locking means comprises a pair of lugs on said catheter hub located respectively on opposite sides of said plane; a pair of lug engaging members, one for each of said lugs; and pivot means connecting said lug engaging members to said needle hub so that they are respectively located on opposite sides of said plane, said pivot means being constructed to permit pivotal movement of said lug engaging members about respective axes that are parallel to said plane.

9. The infusion assembly of claim 4 wherein said upwardly facing wings lie respectively on opposite sides of a plane containing the longitudinal axis of said needle and lying parallel to said axes of said rotation of said hinges with said upwardly directed surfaces thereof lying substantially perpendicular to said last mentioned plane.

10. The assembly of claim 1 wherein the proximal end of said catheter hub has a hollow, cylindrical configuration, said needle hub comprising a distal body portion adapted to be fully received within said proximal end of said catheter hub, and said needle hub further comprises a proximal body portion having said distally facing surface, said distally facing surface surrounding said distal body portion of said needle hub.

* * * * *